United States Patent [19]

Carter et al.

[11] Patent Number: 4,842,997
[45] Date of Patent: Jun. 27, 1989

[54] ENHANCED LUMINESCENT AND LUMINOMETRIC ASSAY

[75] Inventors: Timothy J. N. Carter, Geneva, Switzerland; Carol J. Groucutt; Richard A. W. Stott, both of West Midlands, England; Gary H. G. H. Thorpe, Birmingham, England; Thomas P. Whitehead, Warwickshire, England

[73] Assignee: National Research Development Corporation, London, England

[21] Appl. No.: 551,985

[22] PCT Filed: Feb. 25, 1983

[86] PCT No.: PCT/GB83/00058

§ 371 Date: Oct. 27, 1983

§ 102(e) Date: Oct. 27, 1983

[87] PCT Pub. No.: WO83/03104

PCT Pub. Date: Sep. 15, 1983

[30] Foreign Application Priority Data

Mar. 3, 1982 [GB] United Kingdom ............... 8206263

[51] Int. Cl.$^4$ .................... C12Q 1/68; C12Q 1/28; G01N 33/53

[52] U.S. Cl. ........................... 435/6; 435/7; 435/28; 435/810

[58] Field of Search ............... 435/4, 6, 7, 8, 28, 435/188, 810

[56] References Cited

U.S. PATENT DOCUMENTS 4,375,972  3/1983  Forgione et al. ............... 436/531
4,478,817 10/1984  Campbell et al. ............... 424/7.1
4,598,044  7/1986  Kricka et al. ................... 435/28

FOREIGN PATENT DOCUMENTS 0070686  1/1983  European Pat. Off. .
2008247  5/1979  United Kingdom .
2026690  2/1980  United Kingdom .
2070767  9/1981  United Kingdom .
2070768  9/1981  United Kingdom .
2095830 10/1982  United Kingdom .

OTHER PUBLICATIONS

Whitehead et al., Clinical Chemistry, vol. 25, No. 9, (Sep. 1979), pp. 1531–1546.
Chemical Abstracts, vol. 93, No. 7, Abstract No. 64280u, Slawinska et al.
Whitehead et al. "Nature", 305, pp. 158–159 (1983).
Ham et al. "Analytical Letters", 12(A5), pp. 535–541 (1979).
Ford et al. "Analytical Biochem." 110, pp. 43–48 (1981).
Saunders et al. "Analytical Biochem." 126, pp. 122–130 (1982).
Methods in Enzymology, Bioluminescence and Chemiluminescence, M. DeLuca (Ed.), vol. LVII. pp. 340–342, 385–406, Academic Press, N.Y. (1978).
K. Puget et al., Analytical Biochemistry 79, 447–456 (1977).
T. Kobayashi et al., Agric. Biol. Chem. 45, 1403–1408 (1981).
D. Slawinska et al., Proc. Int. Symp. Anal. Appl. Biolumin. Chemilumin., ed. Schram & Stanley (1979), pp. 239–257.

Primary Examiner—Robert J. Warden
Assistant Examiner—Randall E. Deck
Attorney, Agent, or Firm—Nixon & Vanderhye

[57] ABSTRACT

Assays, e.g. immunoassays, based on the chemiluminescent reaction between a peroxidase enzyme, e.g. horse radish peroxidase, a chemiluminescent 2,3-dihydro-1,4-phthalazinedione, e.g. luminol or isoluminol and an oxidant, e.g. hydrogen peroxide or a perborate, are improved by carrying out the reaction in the presence of a 6-hydroxybenzothiazole, especially 6-hydroxybenzothiazole itself or firefly luciferin. Light emission from the reaction is significantly enhanced by the 6-hydroxybenzothiazole.

24 Claims, 4 Drawing Sheets

ENHANCED LUMINESCENT AND LUMINOMETRIC ASSAY

The present invention relates to an enhanced luminescent or luminometric assay, particularly immunoassay, and to a diagnostic kit designed to facilitate the assay.

Immunoassay is one of the most widely used analytical techniques in the clinical laboratory. At present the majority of immunoassays employ a radioactive isotope, especially iodine-125, as a label. However radioactive isotopes have a number of major disadvantages. First, the method of labelling involves the use of highly radioactive and hence potentially hazardous reagents. Second, the shelf life of the radio-actively labelled substance is often relatively short not only because by its very nature the radioactive isotope is continuously decaying but also because radioactively labelled proteins are often unstable. Third, it is often difficult to label proteins sufficiently to provide a sensitively and rapidly detectable reagent. Fourth, the disposal of radioactively labelled substances is inconvenient.

These disadvantages have stimulated a search for viable alternatives to the radio label. To be suitable as a label a substance should meet at least the following three requirements:

a. it should be detectable both rapidly and in very small quantities when attached to a ligand such as an antigen or an antibody.

b. it should be possible to attach it, without affecting its determination, to a ligand such as an antigen or an antibody, and c. once attached, it should not significantly alter the properties of the ligand.

Some of the most promising alternative labels are either substances which can themselves take part in a reaction resulting in the emission of luminescent light or substances which, on suitable treatment, produce compounds capable of taking part in a luminescent reaction. The luminescent reaction (a chemical reaction that results in the emission of luminescent light) is generally of sufficient duration to enable the light emitted to be detected and measured, and thereby to allow the quantification of the labelled material. On the other hand the measurement of luminescence is a rapid process and may be completed in a matter of seconds rather than the several minutes generally required for the measurement of radioactivity.

Luminescence has been employed in three major luminescent or luminometric immunoassay systems:

a. Organoluminescent or organoluminometric immunoassays wherein chemiluminescent compounds which participate directly in luminescent reactions (ie which are converted to an excited state and then return to a non-excited state with the emission of a photon) have been used to label ligands such as proteins, hormones, haptens, steroids, nucleic acids, metabolites, antigens and/or antibodies. Examples of suitable compounds include luminol and isoluminol;

b. Luminescent catalyst or cofactor immunoassays wherein catalysts or cofactors of luminescent reactions have been used as labels. An example of suitable catalyst is the enzyme peroxidase, and c. Enzyme linked immunoassays wherein luminescent reactions have been used to determine the products formed by the action of enzyme labels on suitable substrates. An example of this type of immunoassay is the determination of antibody linked glucose oxidase by reacting the enzyme/antibody reagent with glucose to form hydrogen peroxide and then measuring the amount of hydrogen peroxide produced by adding luminol under controlled conditions to initiate a luminescent reaction.

The sensitivity of the above immunoassays is determined in part by the lower limit for detection of the label or the product of the label. In the case of luminescent or luminometric immunoassays the sensitivity of the system will depend partially on the light emitted in the luminescent reaction per unit of labelled material. It is one aim of the present invention to provide a luminescent or luminometric immunoassay with an enhanced sensitivity, achieved by determining the labelled material or the product of the label via the present improved luminescent reaction.

Whilst the present improved luminescent reaction is particularly useful in the determination of immunoassay labels or the products thereof, it is by no means limited to this use. Thus it is a further aim of the present invention to provide a luminescent or luminometric assay (immunoassay or otherwise) with an enhanced sensitivity achieved by the incorporation of the present improved luminescent reaction in the assay procedure.

Examples of assays which are not immunoassays but which may incorporate the present luminescent reaction include:

a. An elastase assay based on the release of peroxidase from an insoluble peroxidase-elastin preparation, b. A glucose assay based on co-immobilised glucose oxidase and peroxidase, and c. An assay of a peroxidase enzyme, a 2,3-dihydro-1,4-phthalazinedione, a 6-hydroxybenzothiazole or an oxidant, such as hydrogen peroxide, when these materials are neither labels nor the products of labels.

According to the broadest aspect of the present invention therefore, there is provided an enhanced luminescent or luminometric assay wherein the luminescent reaction is between a peroxidase enzyme, an oxidant, a 6-hydroxybenzothiazole and a chemiluminescent 2,3-dihydro-1,4-phthalazinedione.

Preferably the assay is an immunoassay. The present invention is based upon the surprising finding that the addition of certain 6-hydroxybenzothiazoles to the known 2,3-dihydro-1,4-phthalazinedione/oxidant/peroxidase system significantly enhances the sensitivity of the luminescent reaction produced.

In the present specification the term "enhanced" means that the total light emission of the present luminescent reaction and/or the signal to background ratio of the present luminescent reaction is greater than that achieved by the 2,3-dihydro-1,4-phthalazinedione/oxidant-peroxidase system in the absence of the 6-hydroxybenzothiazole. Only those assays that incorporate a luminescent reaction that is so "enhanced" fall within the scope of the present invention.

It is a particular advantage of the present system that enhancement produced by the addition of the 6-hydroxybenzothiazole is specific for reactions employing the enzyme peroxidase.

A chemiluminescent 2,3-dihydro-1,4-phthalazinedione (DPD) according to this invention may be by any DPD that is converted to an excited state in a chemiluminscent reaction and then returns to a non-excited state with the emission of light Preferably the 2,3-dihydro-1,4-phthalazinedione is of general formula I wherein $R_1$ is amino or substituted amino, and each of $R_2$, $R_3$ and $R_4$ is H, optionally substituted $C_1$-$C_6$ alkyl or alkenyl, hydroxyl, $C_1$-$C_6$ alkoxyl, carboxyl, amino or substituted amino, or $R_2$ is amino or substituted amino and each of $R_1$, $R_3$ and $R_4$ is H, optionally substituted $C_1$-$C_6$ alkyl or alkenyl, hydroxyl, $C_1$-$C_6$ alkoxyl, carboxyl, amino or substituted amino, or $R_1$ and $R_2$ are taken together and are an amino or substituted amino derivative of a benzo group, and each of $R_3$ and $R_4$ is H, optionally substituted $C_1$-$C_6$ alkyl or alkenyl, hydroxyl, $C_1$-$C_6$ alkoxyl, carboxyl, amino or substituted amino.

In the present specification substituted amino incorporates amido.

The form which the chemiluminescent DPD takes in the luminescent reaction of the present invention will depend upon the type of assay under consideration. In the case of assays, such as organoluminescent or organoluminometric immunoassays in which the phthalazinedione is used as a label the chemiluminescent DPD will be a substituted amino derivative of a 2,3-dihydro-1,4-phthal-azinedione wherein the amino group is coupled to a ligand such as a protein, hormone, hapten, steroid, nucleic acid, metabolite, antigen or antibody. The amino group may be coupled directly to the ligand or via a bridging arm. Suitable bridging arms will be well known to those skilled in this art, as is evidenced by the discussion thereof in UK No. 2,008,247A and U.S. Pat. No. 4,104,029. Preferred bridging arms include those derived from hemisuccinate, hemiglutarate, hemimaleate, carboxymethyl, glucuronide, mercaptoacetate and carboxymethyl derivatives. The amino group may be coupled to the ligand by any suitable well known procedure, again certain of these procedures are discussed in UK No. 2,008,247A and U.S. Pat. No. 4,104,029. Preferred coupling procedures include the use of mixed anhydrides, carbodiimides and/or active esters.

Although chemiluminescent DPDs suitable for use in those assays which employ a phthalazinedione as a label may be any substituted amino derivative of a 2,3-dihydro-1,4-phthalazinedione with the amino group coupled to a ligand, the preferred substances are 5-amino-2,3-dihydro-1,4-phthalazinedione (luminol) and 6-amino-2,3-dihydro-1,4-phthalazinedione (isoluminol), in each case with the amino group coupled to a ligand, especially to an antibody.

In the case of assays other than those using phthalazinediones as labels the chemiluminescent DPD will be a 2,3-dihydro-1,4-phthalazinedione, especially of the preferred typed listed above that is not coupled as a ligand. In this case the chemiluminescent DPD may be free in solution or immobilised on a matrix. Particularly preferred materials are luminol and isoluminol.

A 6-hydroxybenzothiazole according to the present invention is any 6-hydroxybenzothiazole (substituted or unsubstituted) that enhances the peroxidase/oxidant/2,3-dihydro-1,4-phthalazinedione luminescent reaction. Preferably, however, the 6-hydroxybenzothiazole is of general formula II wherein R is H, CN or optionally substituted thiazole, and each of $X_1$-$X_3$ is H, optionally substituted $C_1$-$C_6$ alkyl or alkenyl, hydroxyl, substituted hydroxyl, $C_1$-$C_6$ alkoxyl, carboxyl, amino or substituted amino.

In particularly preferred embodiments of the present assay each of $X_1$-$X_3$ is H or $C_1$-$C_6$ alkyl and R is H, CN or a thiazole substituent of general formula III, wherein $X_4$ is COOH and each of $X_5$-$X_7$ is H or $C_1$-$C_6$ alkyl or $X_4$ and $X_5$ are taken together and are O and each of $X_6$-$X_7$ is H or $C_1$-$C_6$ alkyl. Most preferably each of $X_1$-$X_3$ and, where applicable, each of $X_5$-$X_7$ is H. These preferred 6-hydroxybenzothiazoles have been found to give particularly high levels of sensitivity enhancement, especially when the chemiluminescent DPD is luminol or isoluminol.

Any peroxidase enzyme (defined as donor; hydrogen peroxide; Oxidoreductase (EC No. 1.11.1.7) by the International Union of Biochemistry) which catalyses the luminescent reaction of a 2,3-dihydro-1,4-pthalazinedione, especially luminol, may be used in the luminescent reaction of the present invention. Examples include the plant peroxidases. Preferably the enzyme will be horse radish peroxidase (EC No. 1.11.1.7).

The form which the peroxidase enzyme takes in the luminescent reaction of the present invention will depend upon the type of assay under consideration. In the case of assays, especially immunoassays, wherein the peroxidase is used as a label it will be coupled to a ligand such as a protein, hormone, hapten, steroid, nucleic acid, metabolite, antigen or antibody. Generally the peroxidase will be coupled to the ligand via a bridging arm. Suitable bridging arms and coupling procedures will be those described above for chemiluminescent DPDs.

In the case of assays other than those using peroxidase as a label, the enzyme will be in its free form, either in solution or immobilised on a matrix, not coupled to a ligand.

Any oxidant which reacts with a 2,3-dihydro-1,4-phthalazinedione; especially luminol or isoluminol, to cause excitation of the DPD so that it emits light in a luminescent reaction, may be used in the present luminescent reaction. Particularly preferred oxidants are perborate ion and hydrogen peroxide.

In assays, especially immunoassays, which employ a 2,3-dihydro-1,4-phthalazinedione, or a peroxidase enzyme as a label for a ligand, a known quantity of the oxidant will be added to the reaction mixture, generally from a proprietary source. In certain other assays however the amount of oxidant, generally hydrogen peroxide, present will be unknown. In this second type of assay the label will be a substance, often an enzyme such as glucose oxidase or lactate dehydrogenase, which participates in the conversion of a substrate into the oxidant. Thus, in this case, the present luminescent reaction will be used to determine the quantity of labelled ligand by the measurement of the oxidant concentration in the luminescent reaction mixture.

Light emission from the luminescent reaction of the present invention, although depending primarily on the choice of peroxidase, oxidant, 6-hydroxybenzothiazole and chemiluminescant DPD, will also be determined by secondary factors such as temperature, pH, reagent concentration, mixing speed and method of light measurement. To maximise the sensitivity of the present system these secondary factors should be adjusted to obtain the maximum light emission, in a reproducible and easily measurable manner, with the signal to background ratio as high as possible.

The conditions chosen are generally a compromise involving the enzyme or catalytic activity of the peroxidase, the kinetics of the reaction, the apparatus employed, the signal to background ratio and the sensitivity required.

The present inventors have found that in order to achieve optimum results the present luminescent reaction should be conducted under moderate conditions of temperature ranging from 10° to 50° C., and pH, in the range of 6 to 10, most often between 7 and 9. Suitable buffering substances for the method of the present invention are phosphate, tris(hydroxymethyl) aminomethane, 2-amino-2-methyl-1,3-propanediol, acetate, carbonate and borate.

Generally the concentrations of the reagents in the luminescent reaction mixture, with the exception of the material to be determined, are kept constant. The variable factor may be, for example, the concentration of a labelled ligand, a product of a label, an oxidant or unbound peroxidase.

The following reagent concentrations are particularly suitable for use in the present luminescent reaction:

peroxidase 0.1 $\mu$g-5000 mg per liter
oxidant 10 $\mu$mol-300 mmol per liter
6-hydroxybenzothiazole 0.01 mmol-4 mmol per liter
chemiluminescent DPD 0.5 $\mu$mol-200 mmol per liter In performing the present luminescent reaction, certain of the four essential reagents (but omitting at least one) are placed in a sample tube. The luminescent reaction is then triggered by the addition, to the tube, of the missing essential reagent(s). The light emitted may be quantified by a standard measuring device such as a photomultiplier tube the signal from which is fed to and displayed or recorded on a recorder, oscilloscope or scalar. The light may also in some cases be observed by the naked eye or recorded on a photographic plate. Preferably however the light is quantified on a luminometer of the type described in UK Patent Application No. 2025609A.

The luminescent reaction of the present invention may be used in three major types of immunoassay, the distinguishing feature of each being the type of label attached to the ligand. The labels are, a. a substituted amino derivative of a 2,3-dihydro-1,4-phthalazinedione, wherein the amino group is coupled to the ligand, b. a peroxidase enzyme, and c. a substance other than those listed under a. and b. and generally an enzyme such as glucose oxidase or lactate dehydrogenase, which participates in the conversion of a substrate to a material which may be determined by the present luminescent reaction (generally hydrogen peroxide or peroxidase).

In the above immunoassays labelling of the substance to be assayed or of an antibody to such a substance is possible. Depending on the type of label employed, the assay may be either heterogenous or homogeneous. In the former case complex fluids such as serum may be analysed, however, in the latter case, a preliminary extraction or purification step may be necessary.

Typical heterogenous and homogenous luminescent or luminometric immunoassays are outlined below:

1. Heterogenous Luminescent or Luminometric Immunoassay

In this type of immunoassay the substance to be assayed is reacted with an antibody thereto. The free antibody is then separated from the bound antibody. The reaction is quantified by labelling either the antibody, the substance to be assayed or another molecule which can react with the free or bound moieties after separation.

2. Competitive Heterogenous Luminescent Immunoassay

In this case an unknown amount of the substance to be assayed is mixed with a known amount of said substance coupled with a label and a known, but limited, amount of an antibody thereto. A competitive reaction between the labelled and unlabelled substance for the antibody ensues. The complexes between antibody and unlabelled substance and between antibody and labelled substance are separated from the free labelled and unlabelled substance.

The amount of labelled substance bound to antibody is related to the amount of unlabelled substance in the solution being assayed. These quantities may be determined either by measuring the amount of label bound to antibody or by measuring the amount of free labelled substance remaining. Example of this type of assay wherein peroxidase is the label and the antibody is bound to a solid phase, via the walls of a glass test tube, are given in UK No. 2,044,927A.

3. "Two-Site" Heterogeneous Luminometric Immunoassay

In this type of immunoassay the substance to be assayed is first bound to an unlabelled antibody thereto which in turn is bound to a solid phase support, such as plastic. The complex (between antibody and substance) is then treated with a labelled antibody.

Analysis for the labelled antibody in the solid complex obtained may then be effected by separating the solid complex from the solution, and then determining either the amount of label present in the separated solid complex or the amount of label present in the residual labelled antibody dissolved in the solution.

In alternative embodiments of this type of immunoassay the substance to be assayed may either be bound consecutively to the labelled antibody and to the unlabelled, solid supported antibody or be bound to both the labelled and unlabelled antibody in one binding step.

4. Homogeneous Luminescent or Luminometric Immunoassay

This is applicable to immunoassays wherein the label is an amino or a substituted amino derivative of a 2,3-dihydro-1,4-phthalazinedione. It depends upon the light emitted from the free labelled substance of interest (or antibody thereto) being of a different intensity or wavelength to the light emitted from the bound labelled substance of interest (or antibody thereto).

In one example it was found that the intensity of light emitted from the reaction of a (progesterone-isoluminol deriv) conjugate, a haem catalyst and hydrogen peroxide was of a lower intensity than the same reaction performed in the presence of anti-progesterone IgG.

Thus in the assay an unknown progesterone sample was first incubated with a known amount of anti-progesterone IgG. After equilibrium was reached a known amount of (progesterone-isoluminol deriv) conjugate was added, followed by a known amount of haem and hydrogen peroxide. The light emitted was measured and the amount of progesterone present in the unknown sample thereby determined from the standard curve. (The more progesterone present in the unknown sample, the less free IgG is left at equilibrium and the lower is the light yield of the luminescent reaction).

In this way the determination of progesterone may be achieved without the requirement of a separation step.

In all of the above immunoassays the quantifying, detecting or locating step may be the luminescent reaction of the present invention.

The antibodies employed in the above immunoassays may be purchased commercially or prepared by known immunological techniques. The antibodies may be in the form of a complex mixture of antibodies or they may be one or more monoclonal antibodies, Only a small volume of antibody is generally required and it is maintained at the conditions of pH, ionic strength and temperature appropriate for its activity.

Antibodies to the following non-exhaustive list of substances may be usefully employed in immunoassays utilising the present luminescent reaction: proteins such as insulin, alphafetoprotein and ferritin, hormones such as growth hormone, parathyroid hormone, follicle stimulating hormone, luteinising hormone, thyroid stimulating hormene, adrenocorticotrophic hormone, glucagon, prolactin and calcitonin, haptens/steroids such as estriol, progesterone and cortisol, drugs such as digoxin, antigens such as cell surface antigens and carcino embryonic antigen and antibodies such as mumps virus antibody, human immunoglobulin G (IgG) rabbit IgG, sheep IgG, guinea pig IgG, donkey IgG and human immunoglobulins E and M.

The luminescent reaction of the present invention may also be used in assays other then the immunoassays described above. These include:

1. The assay of elastase based on the release of peroxidase from an isoluble peroxidase elastin preparation In this assay a solid elastin-peroxidase conjugate is incubated with varying amounts of hte enzyme elastase. After a pre-determined period unreacted conjugate is removed by centrifugation and the supernatant is assayed for unbound peroxidase.

The amount of unbound peroxidase present in the supernatant is related to be elastase activity in the sample tested.

2. The assay of proteinase based on the release of isluminol from a synthetic peptide substrate In this assay immobilised synthetic peptide substrate, Affi-gel 10-Ala-Ala-Ala-Phe-isoluminol, is treated with varying quantities of the proteinase. After a predetermined period unreacted substrate is removed by centrifugation and the supernatant is assayed for islouminol. The amount of isoluminol present in the supernatant is related to proteinase activity in the sample tested.

3. The assay of glucose based on co-immobilised glucose oxidase and peroxidase

In this assay glucose oxidase and peroxidase are co-immobilised on a support, eg sepharose of plastic tubes. To this is added a solution of luminol and 6-hydroxybenzothiazole. Finally a solution of glucose is added and the light emission recorded. Light emission is directly related to the amount of glucose in solution.

The major use of the present assay and luminescent reaction will be in clinical laboratories and doctors' surgeries. It is usual for such laboratories and/or surgeries to obtain the materials to be used in a given assay procedure in the form of an assay kit.

Accordingly the present invention also provides an assay kit for use in the enhanced luminescent or luminometric assay of the present invention comprising:

a. a peroxidase enzymy,
b. a 6-hydroxybenzothiazole, and
c, a chemiluminescent 2,3-dihydro-1,4-phthalazinedione.

The test kit may also contain an oxidant, but in many cases this material may either be provided separately or be the substance to be assayed.

Preferably the peroxidase enzyme, the oxidant, the 6-hydroxybenzothiazole and the chemiluminescent DPD will be those listed above as preferred for use in the present assay. In one particularly preferred embodiment of the present assay kit at least one of the peroxidase enzyme and the chemiluminescent DPD is coupled to an antibody to the substance to be assayed.

Optionally the assay kit may also contain one or more standard solutions each containing a known amount of the substance to be assayed, and/or one or more of the preferred buffer solutions. Conveniently the assay kit may also include a reaction vessel suitable for use in conjunction with the apparatus used for the determination of the light emitted in the course of carrying out the assay. Also a mixing device may be included in the assay kit, for use in ensuring adequate admixture of the reagents.

The assay, luminescent reaction and assay kit of the present invention will now be described by way of example only with particular reference to the figures in which.

MATERIALS AND METHODS

Reagents

Horse radish peroxidase (HRP; Reinheit Zahl (the ratio of A403 to A250; RZ) approximately 1.0) was obtained from Hughes and Hughes Ltd, Romford, Essex, UK, and was purified by gel-filtration using a 2.6 cm×40 cm AcA 34 column (LKB Instruments Ltd, South Croydon, Surrey, UK). The column was eluted using 0.015 mol/$_1$ phosphate buffer, pH7.2, containing 0.15 mol/$_1$ NaCl: the purified peroxidase obtained had an RZ of approximatily 3.0.

Alpha fetoprotein (AFP), rabbit anti-human AFP (code 100-008) and rabbit and anti-human AFP/HRP conjugate were obtained from Dako Products, Mercia Brocades Ltd, Brocades House, Pyrford Road, West Byfleet, Weybridge, Surrey.

Thyroxine (T4), rabbit anti-T4 coated vials and T4/HRP conjugate were obtained from the Boehringer Corporation, Lewes, Sussex, UK.

Rubella virus (human) coated beads and anti-human IgG (goat)/HRP conjugate were obtained from Abbott Laboratories Ltd, Diagnostic Division, Bright Hill Parade, Basingstoke, Hampshire.

D-Firefly luciferin (4,5-dihydro-2-(6-hydroxy-2-benzothiazoly)-4-thiazole carboxylic acid, product No. L9504, synthetic crystalline), bovine serum albumin (BSA; product A4503) and 2-amino-2-methyl-1,3-propandiol (AMP; product No. A9754) were obtained from the Sigma Chemical Co, Poole, Dorset, UK.

Liminol (5-amino-2,3-dihydro-1,4-phthalazinedione) and isoluminol (6-amino-2,3-dihydro-1,4-phthalazinedione) were obtained from the Sigma Chemical Co, Fancy Road, Poole, Dorset, UK. The monosdium salt of luminol was prepared as described previously (Ham et al., *Anal. Lett.* 1979, 12, 535).

7-Dimethylaminonaphthalene-1,2-dicarboxylic acid hydrazide (formula I, $R_1$ and $R_2$ are taken together and are a dimethylamino substituted benzo group, $R_3=R_4=H$) was obtained from Boehringer Mannheim.

N-(6-Aminohexyl-N-ethyl) isoluminol was obtained from LKB, Finland.

Tween-20 was obtained from Koch-Light Laboratories Ltd, Colnbrook, Bucks, UK.

2,2'-Azinodi-(3-ethylbenzthiazoline-6-sulphonate) (ABTS) was obtained from the Boehringer Corporation, Lewes, Sussex, UK.

Elastin, elastase, and glucose oxidase were obtained from the Sigma Chemical Co, Dorset. Cyanogen bromide was obtained from the Aldrich Chemical Co, Gillingham.

6-Hydroxybenzothiazole was obtained as a gift from the Chemistry Dept. University of Birmingham.

2-Cyano-6-hydroxybenzothiazole and dehydroluciferin were prepared by the procedures described in Methods of Enzymology, Vol. LVII "Bioluminescence and Chemiluminescence" Ed. M. DeLuca, Academic Press, London, 1978, pp 15–28.

Oxyluciferin was prepared by the process of Bitler et al., *Arch. Biochem. Biophys.*, 1957, 358.

All other reagents were of analytical grade where possible and were supplied by BDH Ltd, Poole, Dorset, UK. Freshly glass distilled water was further purified by passing down a 2.6 cm×40 cm column of Analytical Equipment Chemiluminescent reactions were carried out in 10 mm×10 mm, 4 ml. volume plastic disposable cuvettes (W Sarstedt Ltd, Leicester, LE3 1UQ, UK). The light emmitted was quantitated via a luminemeter described previously (Carter et al., UKPA 2025609A), incorporating a modification allowing several cuvettes to be successively positioned, accurately and reproducibly, in front of the photocathode of the photomultiplier tube. Results were displayed on a fast potentiometric chart recorder (Type PM 8202; Philips, Eindhoven, Netherlands; full scale deflection time, less than 0.25 sec).

EXAMPLE 1-LUMINESCENT ASSAY OF PEROXIDASE

In initial experiments, 10μof firefly luciferin (0.01–1.0 g/l in 0.1 mol/l AMP buffer pH 8.9 containing 1 mmol/l $MgCl_2$), 10 μl of luminol (0.0003–30 g/l in water), 10 μl of $H_2O_2$ (3–300 mmol/l in water) and 10 μl of HRP (0.05–5000 mg/l in 0.015 mol/l phosphate buffer, pH 7.2, containing 0.15 mol/l NaCl, 2 g/l BSA and 0.5 g/l Tween 20) were each placed in separate corners of a 10 mm×10 mm plastic cuvette without allowing them to mix. The luminescent reaction was then initiated by injecting 1 ml. of buffer (0.1 mol/l glycine-NaOH, pH 8.6 to 12.5; 0.1 mol/l glycyglycine-NaOH, pH 7.5 to 9.0: Tris-HCl, pH 7.2 to 8.5; or 0.1 mol/l AMP, pH 7.5 to 9.5) and the peak light output measured.

After optimisation of the concentrations of reagents employed in this assay using the analytical procedure described above, a simplified assay procedure was employed for the measurement of low HRP concentrations. Sodium luminol (50 mg) and hydrogen peroxide (62μl; 30% w/v) were added to 200 ml. Tris (0.01 mol/l; pH 8.0) buffer containing potassium chloride (0.15 mol/l). The solution was prepared several hours before use and used to initiate the luminescent reaction. 10μof firefly luciferin (1 mg/ml) in Tris buffer (0.01 mol/l; pH 8.0) was placed in one corner of a cuvette and 10μl of anti-AFP/HRP conjugate was placed in another corner. The reaction was initiated by injection of the luminol/$H_2O_2$ reagent (0.9 ml). The light emission after 30 sec. or peak light output was measured.

EXAMPLE 2

The simplified procedure of Example 1 was repeated except that 6-hydroxybenzothiazole in DMSO replaced firefly luciferin.

EXAMPLE 3

The simplified procedure of Example 1 was repeated except that 2-cyano-6-hydroxybenzothiazole in DMSO replaced firefly luciferin.

EXAMPLE 4

The simplified procedure of Example 1 was repeated except that luminol was replaced by N-(6-aminohexyl)-N-ethylisoluminol.

EXAMPLE 5

The simplified procedure of Example 1 was repeated except that luminol was replaced by isoluminol.

EXAMPLE 6

The simplified procedure of Example 1 was repeated except that luminol was replaced by 7-dimethylamino napththalene-1,2-dicarboxylic acid hydrazide (9-dimethylamino-2,3-dihydrobenzo [f] phthalazine-1,4-dione) and the phthalazinedione/$H_2O_2$ was diluted 1 in 10 before use.

EXAMPLE 7

The simplified procedure of Example 1 was repeated except that hydrogen peroxide was replaced by soldium perborate.

EXAMPLE 8—ASSAY OF ANTI—AFP/HRP CONJUGATE

Soldium luminol (50 mg) and hydrogen peroxide (62μl: 30% w/v) were added to 200 ml Tris (0.01 mol/l: pH 8.0) buffer containing potassium chloride (0.15 mol/l). The solution was prepared several hours before use and used to initiate the luminescent reaction. 10μl of firefly luciferin (1 mg/ml) in Tris buffer (0.01 mol/l: pH 8.0) was placed in one corner of a cuvette and 10μl of anti-AFP/HRP conjugate was placed in another corner. The reaction was initiated by injection of the luminol/$H_2O_2$ reagent (0.9 ml). The light emmission after 30 sec. or the peak light output was measured.

Figure 1:
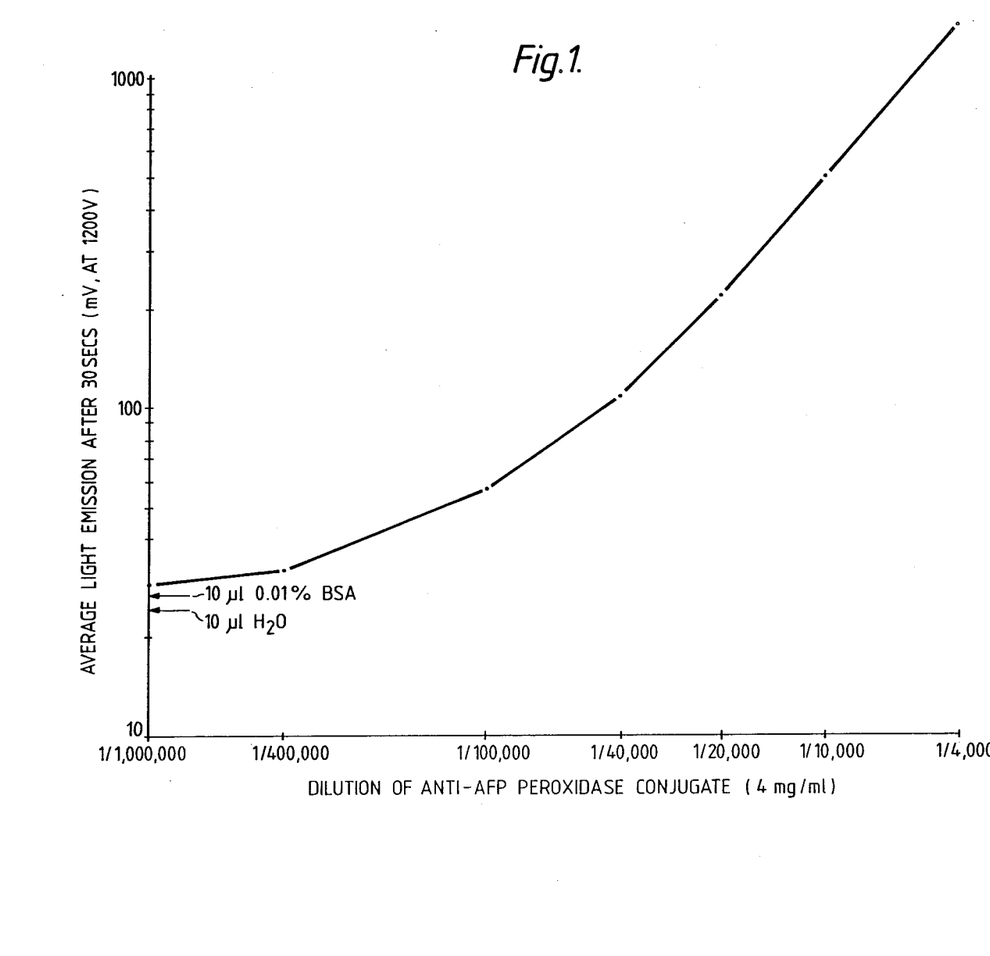
FIG. 1 is a dilution curve for peroxidase labelled anti-AFP.

A dilution curve for peroxidase labelled anti-AFP is given in FIG. 1. Signal to background ratios for this reaction are given in Table 1.

EXAMPLE 9 (COMPARATIVE)

The procedure of Example 8 was followed except that no firefly luciferin was used. Signal to background ratios for this reaction are given in Table 1.

TABLE

The Measurement of Signal to Background Ratio of the Luminol, Hydrogen Peroxide, Anti-AFP/HRP Reaction at pH 8.0 in the Absence and Presence of Firefly Luciferin

|  |  | Luminol/ $H_2O_2$ | Luminol/$H_2O_2$/ Firefly Luciferin |
|---|---|---|---|
| Peak light emission | Sample | 135 | 1420 |
|  | Blank | 15 | 170 |
|  | Signal/Background ratio | 9 | 8.4 |
| Light emission after 30 secs | Sample | 35 | 540 |
|  | Blank | 15 | 20 |
|  | Signal/Background ratio | 2.3 | 27 |

Note: 1
Light emission is measured as output (mV) at a photomultiplier voltage of 1,200 v. The sample used was a 1:10,000 dilution of anti-AFP/HRP conjugate.
Note: 2
The measurement of light emission after 30 seconds enabled the signal to background ratio to be increased by a factor of 3 compared with the signal to background ratio abtained for peak light emission in the absence of firefly luciferin.

EXAMPLE 10—ASSAY OF AFP a. (1) To a 500 ml wide mouthed glass bottle was added 125 ml glycine/NaOH buffer (0.1 nol/l, pH 8.8) and 0.25 g BSA. The solution was then mixed for 2 hrs on a roller mixer at 20° C. After this time the bottle (and its lid) was rinsed with glycine buffer (3×50 ml) to remove any unbound albumin and finally was allowed to drain. (2) 1000 Polystyrene beads were washed with Lipsol (Trade Mark, 1%, 500 ml) for 30 min. After washing with distilled water the beads were placed in a Buchner flask, together with 200 ml glycine buffer, and degassed. (3) Glycine buffer (400 ml) was transferred to the precoated glass bottle and rabbit anti-human AFP (1.5 ml) was added. The solution was well mixed and then the degassed beads were added. The whole was mixed on the roller mixer for 6 hrs at 20° C. (4) After 6 hrs the glycine buffer-antibody solution was decanted and the beads were twice with 400 ml PBS (0.015 mol/l phosphate, 0.15 mol/l NaCl, pH 7.2). After decanting the second PBS wash, a solution of BSA (0.5%) in PBS (400 ml) was added. Once again the whole was mixed on the roller mixer at 20° C. After 30 min. the PBS-albumin solution was removed and acetate buffer (0.1 mol/l, pH 4.2, 400 ml) containing Tween 20. (Trade Mark 0.01%) was added. Mixing was effected for 10 min and then the acetate buffer was replaced by PBS buffer containing 0.05% Tween (2×400 ml). Finally the PBS was decanted and the beads were dried on filter paper at 20° C. for 30 min. The beads were stored in screw capped bottles at 4° C.

b. (1) Sufficient antibody coated beads (step a. above) in PBS were degassed for 15–30 mins. (2) 50μl of a standard or specimen containing AFP was added to a cuvette together with 0.95 ml PBS/BSA/Tween (phosphate 0.015 mol/l; NaCl 0.15 mol/l; BSA 0.25; Tween 20 0.05%: pH 7.2). the solution was warmed to 37° C. and then incubated with the beads for 1 hr. (3) the solution was then decanted and the beads were washed with PBS/Tween (200 ml for 15 sec, then 200 ml for 5 min). (4) The beads were then incubated with 0.9 ml 1:1000 dilution of rabbit anti-human AFP/HRP conjugate for 1 hr. (The conjugate was diluted in PBS/BSA/Tween and, prior to addition to the beads, was warmed to 37° C.)

c. (1) The solution was once again decanted and the beads were washed with deionised, distilled water for 2 min. After decanting the water the beads were carefully transferred to cuvettes (one per cuvette). (2) Into the corner of each cuvette was also placed 10μl of firefly luciferin (1 mg/ml) in Tris buffer (0.01 mol/l, pH 8.0).

Figure 2:
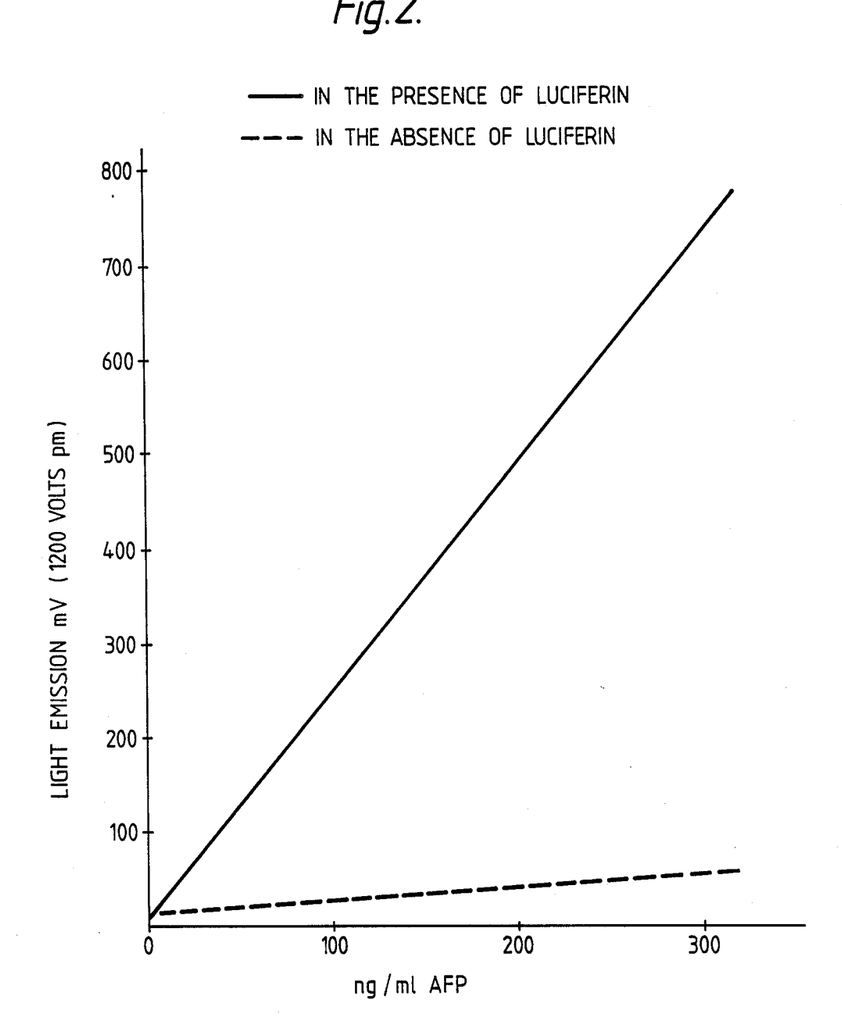
FIG. 2 is the light emission of rabbit anti-human AFP/HRP, bound to AFP, immobilised onto antibody coated beads, in the presence and absence of firefly luciferin.
Figure 3:
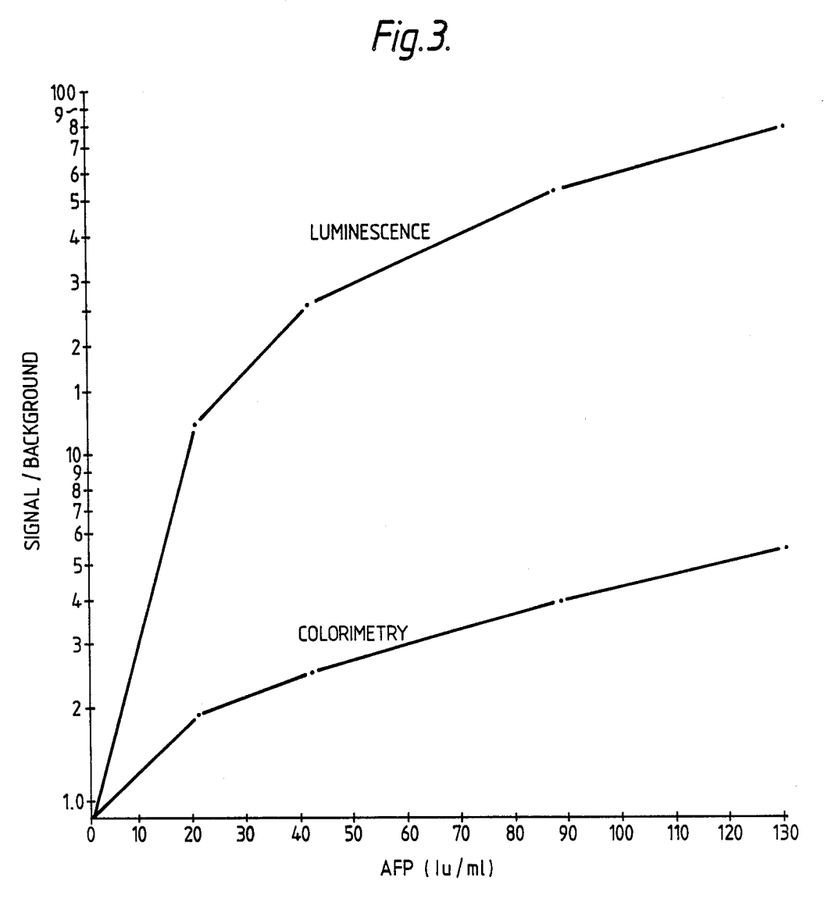
FIG. 3 is a comparison of the signal/background ratio for the luminescent and colorimetric determination of AFP.

The luminescent reaction was initiated by the injection of 0.9 ml luminol/$H_2O_2$ solution (sodium luminol (50 mg), $H_2O_2$ (62μl; 30% w/v), Tris (0.01 mol/l, pH 8.0, 200 ml), potassium chloride (0.15 mol/l)). The light emission after 30 sec was measured and is given in FIG. 2. A comparison of the signal/background ratio with increasing AFP concentration is given in FIG. 3.

EXAMPLE 11 (COMPARATIVE)

The procedure of Example 10 was repeated except that no firefly luciferin was used in the luminescent reaction. The light emission after 30 sec was measured and is given in FIG. 2.

EXAMPLE 12 (COMPARATIVE)

The procedure of Example 10 was repeated except that the peroxidase labelled anti-AFP was determined by the following colorimetric method.

ABTS (0.55 g) was dissolved in acetate buffer (500 ml, 0.1 ml/l, pH 4.2) containing 0.01% Tween 20. Hydrogen peroxide (2.83 ml), 100 vols, 30% w/v) was diluted to 100 ml with distilled water. These stock solutions were stored at 4° C. Immediately prior to use 1 ml of the $H_2O_2$ solution was mixed with 100 ml of the ABTS solution and 0.9 ml of the resulting mix was incubated with each bead, (from step c (1) of Example 10), at 37° C. for 30 min with agitation. After this incubation period the absorbance at 405 nm was measured againsts working enzyme substrate solution. A comparison of the signal/background ratio with increasing AFP concentration is given in FIG. 3,

EXAMPLE 13

The assay of Example 10 was repeated except that firefly luciferin was replaced by 6-hydroxybenzothiazole in DMSO.

EXAMPLE 14

The assay of Example 10 was repeated except that firefly luciferin was replaced by 2-cyano-6hydroxybenzothiazole in DMSO.

EXAMPLE 15—ASSAY OF T4

T4 was assayed using a competitive enzyme linked immunosorbent assay. A mixture of unlabelled T4 (sample or standard) and T4/HRP conjugate was incubated with a limited quantity of anti-T4 coated tubes.

Figure 4:
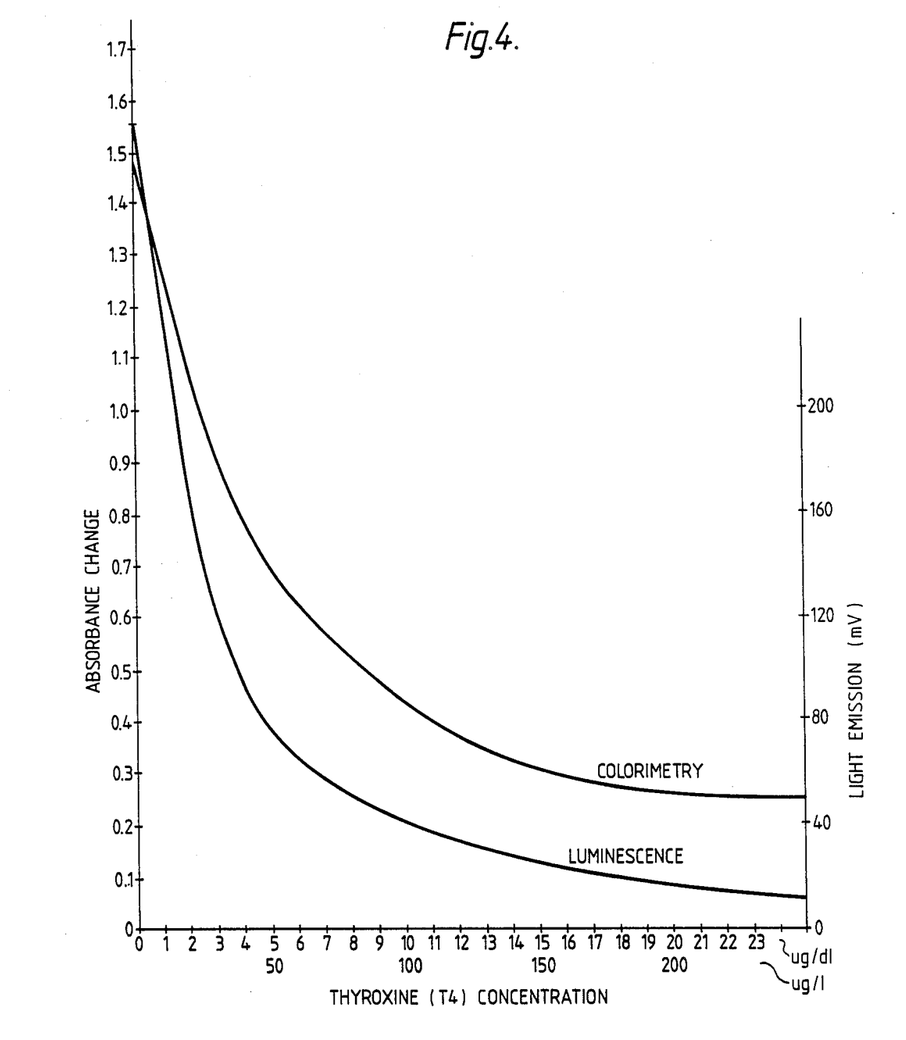
FIG. 4 is a comparison of the light emission and absorbance changes with increasing T4 concentration in the liminescent and colorimetric determination of T4.

After equilibrium had been reached the tubes were washed to remove unbound components and then 10μl of firefly luciferin (1 mg/ml) in Tris buffer (0.01 mol/l, pH 8.0 ) was placed into each tube. The luminescent reaction was initiated by the injection of 0.9 ml luminol/$H_2O_2$ solution (sodium luminol (50 mg), $H_2O_2$ (62μl; 30% w/v), Tris (0.01 mol/l, pH 8.0, 200 ml), potassium chloride (0.15 mol/l)). The light emission after 30 sec was measured. A comparison of the light emission change with increasing T4 concentration is given in FIG. 4.

EXAMPLE 16 (COMPARATIVE)

T4 was assayed using a competitive enzyme linked immunosorbent assay. A mixture of T4 (sample or standard) and T4/HRP conjugate was incubated with a limited quantity of rabbit anti-T4 coated onto tubes.

After equilibrium had been reached and excess reagents removed, 1.0 ml phosphate/citrate buffer (pH 5.0) containing 9.1 mmol/l ABTS and 1.47 mmol/l sodium perborate was added and used to determine the quantity of antibody-T4-HRP complex in each tube by incubating for 60 min at 25 C. A comparison of the absorbance change at 420 nm with increasing T4 concentration is givent in FIG. 4.

EXAMPLE 17—ASSAY OF ANTI-RUBELLA IgG

A test specimen containing anti-rubella IgG was incubated with rubella virus (human) coated beds in Tris buffer. After washing to remove unreacted components the beads were incubated with anti-human IgG (goat)/HRP comjugate, again in Tris buffer.

The solution was decanted and the beads were washed with deionised distilled water. After removing the washed beads from the water they were transferred to cuvettes (one per cuvette).

Into the corner of each cuvette was also placed 10μl of firefly luciferin (1 mg/ml) in phosphate buffer (0.1 mol/l, pH 8.0). The luminescent reaction was initiated by the injection of 0.9 ml luminol/$H_2O_2$ solution (sodium luminol (50 mg), $H_2O_2$ (62μl; 30% w/v), Tris (0.01 mol/l, pH 8.0, 200 ml), potassium chloride (0.15 mol/l)). The light emission after 30 sec was measured and is given in Table 2. A comparison of the signal/background ratio with increasing anti-rubella IgG concentrations is given in Table 3.

EXAMPLE 18 (COMPARATIVE)

A test speciment containing anti-rubella IgG was incubated with rubella virus (human) coated beads in Tris buffer. After washing to remove unreacted components the beads were incubated with anti-human IgG (goat)/HRP comjugate, again in Tris buffer.

The solution was decanted and the beads were washed with deionised, distilled water. After removing the washed beads from the water they transferred to cuvettes (one per cuvette).

The amount of labelled antibody bound to each bead was determined by adding o-phenylenediamine/$H_2O_2$ in citrate-phosphate buffer to the cuvette. After 0.5 hr the reaction was stopped by the addition of hydrochloric acid and the absorbance at 492 nm was measured. Results are given in Table 2. A comparison of the signal/background ratio with increasing anti-rubella IgG comcentration is given in Table 3.

TABLE 2

| Sample of anti-rubella IgG | Luminescence Light emitted after 30 sec (mv,1200 volts PM) | Colorimetry Absorbance at 492 nm after 30 mins |
| --- | --- | --- |
| Negative control | 8 | 0.06 |
| Low Positive Control (HAI titre approx 10) | 92 | 0.46 |
| High positive Control (HAI titre approx 80) | 455 | 1.51 |

TABLE 3

| Sample of anti-rubella IgG | Signal/Background ratio Luminescence | Signal/Background ratio Colorimetry |
| --- | --- | --- |
| Negative control | 1 | 1 |
| Low Positive Control (HAI titre approx 10) | 11.2 | 8.5 |
| High Positive Control (HAI titre approx 80) | 55 | 28 |

EXAMPLE 19–ASSAY OF ELASTASE

Horseradish peroxidase was conjugated to powdered elastin by the method of G C Saunders etal, *Analytical Biochemistry*, 1982, 126, 122). 1 ml of elastin-peroxidase suspension was washed and equilibrated in 2 ml of 0.0 mol/l Tris buffer (pH 9), containing $CaCl_2$ (2 mmol/l) for 0.5 hr at 37° C. The conjugate was clastase (0–100 ng/ml) in Tris-$CaCl_2$ buffer were added and incubated at 37° C. with the elastin-HRP. After 60 mins unreacted HRP-conjugate was removed by centrifugation and an aliquot of supernatant transferred and recentrifuged. 200μl of supernatant was removed and placed in a cuvette and light emission was initiated by the addition of 0.91 ml luminol/$H_2O_2$/6-hydroxybenzothiazole solution (sodium luminol (50 mg) $H_2O_2$ (62μl; 30% w/v), 6-hydroxybenzothiazole (2 ml, 1 mg/ml in DMSO), in 200 ml. Tris buffer (0.1 mol/l, pH 8.0). The light emission after 30 sec was measured.

EXAMPLE 20

The assay of Example 19 was repeated except that 2-cyano-6-hydroxybenzothiazole replaced 6-hydroxybenzothiazole.

EXAMPLE 21

The assay of Example 19 was repeated except that firefly luciferin replaced 6-hydroxybenzothiazole.

EXAMPLE 22—GLUCOSE ASSAY BASED ON CO-IMMOBILISED GLUCOSE OXIDASE AND PEROXIDASE

Glucose oxidase (5 mg; Sigma) and horse radish peroxidase (5 mg, Sigma) were co-immobilised onto cyanogen bromide activated Sepharose (Pharmacia, UK) by the procedure of Ford and DeLuca, *Anal Biochem*, 1981, 110,43. The immobilised enzymes were suspended in phosphate buffer (0.1 mol/l, pH 7.0). A suspension of the immobilised enzymes (100 gm/l, 50μl) were added to 1 ml of aqueous luminol solution (25 mg per 100 ml) and 50μl of 6-Hydroxybenzothiazole (1 mg/ml in DMSO) contained in a cuvette. A 10μl aqueous sample of a glucose containing solution was then added, the cuvette contents mixed, and the light emission recorded. Peak light emission was linear bewteen 50 and 500 nmol of glucose. Alternatively the glucose oxidase and peroxidase can be immobilised onto the surface of plastic supports (eg Leon et al, *Clin Chem*, 1977, 23, 1556.

EXAMPLE 23

The assay of Example 22 was repeated except that 2-cyano-6-hydroxybenzothiazole replaced 6-hydroxybenzothiazole.

EXAMPLE 24

The assay of Example 22 was repeated except that firefly luciferin replaced 6-hydroxbenzothiazole.

EXAMPLE 25

The simplified assay of Example 1 was repeated except that firefly luciferin was replaced by oxyluciferin.

EXAMPLE 26

The simplified assay of Example 1 was repeated except that firefly luciferin was replaced by dehydroluciferin.

We claim:

1. In a luminescent or luminometric assay which comproses carrying out a chemiuluminescent reaction between a peroxidase enzyme, an oxidant, and a chemiluminescent 2,3-dihydro-1,4-phthalazinedione and measuring or detecting the chemiluminescence thereby produced, the improvement wherein the reaction is carried out in the presence of a 6-hydroxybenzothiazole.

2. An assay according to claim 1 wherein the chemiluminescent 2,3-dihydro-1,4-phthalazinedione is of general formula I wherein $R_1$ is amino or substituted amino, and each of $R_2$, $R_3$ and $R_4$ is H, $C_1-C_6$ alkyl or alkenyl, hydroxyl, $C_1-C_6$ alkoxyl, carboxyl, amino or substituted amino, or $R_2$ is amino or substituted amino and each of $R_1$, $R_3$ and $R_4$ is H, $C_1-C_6$ alkyl or alkenyl, hydroxyl, $C_1-C_6$ alkoxyl, carboxyl, amino or substituted amino, or $R_1$ and $R_2$ are taken together and are an amino or substituted amino derivative of a benzo group, and each of $R_3$ and $R_4$ is H, $C_1-C_6$ alkyl or alkenyl, hydroxyl, $C_1-C_6$ alkoxyl, carboxyl, amino or substituted amino.

3. An assay according to claim 1 wherein the chemiluminescent 2,3-dihydro-1,4-phthalazinedione is selected from the group consisting of luminol and isoluminol.

4. An assay according to claim 1 wherein the peroxidase enzyme is a plant peroxidase.

5. An assay according to claim 4 wherein the peroxidase enzyme is horseradish peroxidase.

6. An assay according to claim 1 wherein the oxidant is perborate ion or hydrogen peroxide.

7. An assay according to claim 1 wherein either the peroxidase enzyme or the chemiluminescent 2,3-dihydro-1,4-phthalazinedione is coupled to a ligand.

8. An assay according to claim 7 wherein the ligand is an antibody.

9. An assay according to claim 7 wherein the ligand is selected from the group consisting of a protein, a hormone, a hapten, a steroid, a nucleic acid, a metabolite and an antigen.

10. An assay according to claim 1 which is an immunoassay.

11. An assay according to claim 1 wherein the 6-hydroxybemnzothiazole is of the general formula wherein R is H, CN, thiazole or substituted thiazole and each of $X_1$ to $X_3$ is H, $C_1-C_6$ alkyl or alkenyl, hydroxyl, $C_1-C_6$ alkoxyl, carboxyl, amino or substituted amino.

12. An assay according to claim 11 wherein each of $X_1-X_3$ is H or $C_1-C_6$ alkyl, and R is H, CN or a thiazole substituent of general formula III wherein $X_4$ is COOH and each of $X_5-X_7$ is H or $C_1-C_6$ alkyl, or $X_4$ and $X_5$ are taken together and are O and each of $X_6-X_7$ is H or $C_1-C_6$ alkyl.

13. An assay according to claim 12 wherein each of $X_1-X_3$ is H and each of $X_5-X_7$ is H.

14. An assay kit for use in a luminescent or luminometric assay comprising in separate containers:
(a) a peroxidase enzyme
(b) a chemiluminescent 2,3-dihydro-1,4-phthalazinedione which is coreactable with said peroxidase enzyme and with an oxidant in a chemiluminescent reaction and
(c) a 6hydroxybenzothiazole, said component (c) being in unconjugated form, said peroxidase enzyme being the sole enzyme in the kit.

15. An assay kit according to claim 14 wherein the chemiluminescent 2,3-dihydro-1,4-phthalazinedione is of general formula I wherein $R_1$ is amino or substituted amino, and each of $R_2$, $R_3$ and $R_4$ is H, $C_1-C_6$ alkyl or alkenyl, hydroxyl, $C_1-C_6$ alkoxyl, carboxyl, amino or substituted amino, or $R_2$ is amino or substituted amino and each of $R_1$, $R_3$ and $R_4$ is H, $C_1$-$C_6$ alkyl or alkenyl, hydroxyl, $C_1$-$C_6$ alkoxyl, carboxyl, amino or substituted amino, or $R_1$ and $R_2$ are taken together and are an amino or substituted amino derivative of a benzo group, and each of $R_3$ and $R_4$ is H, $C_1$-$C_6$ alkyl or alkenyl hydroxyl, $C_1$-$C_6$ alkoxyl, carboxyl, amino or substituted amino.

16. An assay kit according to claim 15 wherein the chemiluminescent 2,3-dihydro-1,4-phthalazinedione is selected from the group consisting of luminol and isoluminol.

17. An assay kit according to claim 14 wherein the peroxidase enzyme is a plant peroxidase.

18. An assay kit according to claim 17 wherein the peroxidase enzyme is horseradish peroxidase.

19. An assay kit according to claim 14 further comprising an oxidant.

20. An assay kit according to claim 19 wherein the oxidant is selected from the gourp consisting of perborate ion and hydrogen peroxide.

21. An assay kit according to claim 14 wherein either the peroxidase enzyme of the chemiluminescent 2,3-dihydro-1,4-phthalazinedione is coupled to an antibody to the substance to be assayed.

22. An assay kit according to claim 14 wherein the 6-hydroxybenzothiazole is or the general formula wherein R is H, thiazole or substituted thiazole and each of $X_1$ to $X_3$ is H, $C_1$-$C_6$ alkenyl, hydroxyl, $C_1$-$C_6$ alkoxyl, carboxyl, amino or substituted amino.

23. An assay kit according to claim 22 wherein each of $X_1X_3$ is H or $C_1$-$C_6$ alkyl, and R is H, CN or a thiazole substituent of general formula III wherein $X_4$ is COOH and each of $X_5$-$X_7$ is H or $C_1$-$C_6$ alkyl, or $X_4$ and $X_5$ are taken together and are O and each of $X_6$-$X_7$ is H or $C_1$-$C_6$ alkyl.

24. An assay kit according to claim 23 wherein each of $X_1$-$X_3$ is H and each of $X_5$-$X_7$ is H.

* * * * *